US010753129B2

(12) United States Patent
Gunnsteinsson et al.

(10) Patent No.: US 10,753,129 B2
(45) Date of Patent: Aug. 25, 2020

(54) HINGE FOR ORTHOPEDIC DEVICE

(71) Applicant: OSSUR ICELAND EHF, Reykjavik (IS)

(72) Inventors: Larus Gunnsteinsson, Reykjavik (IS);
Bjorn Omarsson, Reykjavik (IS);
Sindri Pall Sigurdsson, Reykjavik (IS);
Henry Hsu, Foothill Ranch, CA (US)

(73) Assignee: OSSUR ICELAND EHF, Reykjavik (IS)

( * ) Notice: Subject to any disclaimer, the term of this patent is extended or adjusted under 35 U.S.C. 154(b) by 167 days.

(21) Appl. No.: 16/058,024

(22) Filed: Aug. 8, 2018

(65) Prior Publication Data

US 2019/0048923 A1 Feb. 14, 2019

Related U.S. Application Data

(60) Provisional application No. 62/543,201, filed on Aug. 9, 2017.

(51) Int. Cl.
| *E05D 1/02* | (2006.01) |
| *E05D 1/00* | (2006.01) |
| *A61F 5/01* | (2006.01) |
| *F16C 11/12* | (2006.01) |

(52) U.S. Cl.
CPC .............. *E05D 1/02* (2013.01); *E05D 1/00* (2013.01); *A61F 5/0102* (2013.01); *A61F 5/0125* (2013.01); *F16C 11/12* (2013.01)

(58) Field of Classification Search
CPC ... E05D 1/00; E05D 1/02; F16C 11/12; A61F 5/0125; A61F 5/0102

USPC .................................. 602/16; 403/291, 220
See application file for complete search history.

(56) References Cited

U.S. PATENT DOCUMENTS

| 1,142,045 A | 6/1915 | McLeod |
| 1,446,230 A | 2/1923 | Welter |
| 2,980,110 A | 4/1961 | Brumfield et al. |
| 3,167,207 A * | 1/1965 | Kruger ...................... E05D 1/02 220/847 |

(Continued)

FOREIGN PATENT DOCUMENTS

| DE | 3245471 A1 | 3/1984 |
| DE | 3637879 A1 | 5/1988 |

(Continued)

OTHER PUBLICATIONS

International Search Report from PCT Application No. PCT/US2018/045698, dated Nov. 27, 2018.

(Continued)

*Primary Examiner* — Jeffrey O'Brien
(74) *Attorney, Agent, or Firm* — Workman Nydegger

(57) ABSTRACT

A hinge has a hinge body forming an articulating section extending between a first end and a second end of the hinge. The articulating section is adapted to bend from a neutral axis when the first and second ends are parallel to an angular range in which the first end is arranged among a plurality of angles within the angular range relative to the second end. The hinge body may define a receptacle along the articulating section, and an insert may be provided for insertion into the receptacle. The insert can modify the stiffness of the hinge in the angular range and is arranged parallel to the neutral axis.

18 Claims, 8 Drawing Sheets

(56) References Cited

U.S. PATENT DOCUMENTS

| | | | |
|---|---|---|---|
| 3,531,807 A * | 10/1970 | Devito | A41D 27/06 |
| | | | 2/256 |
| 3,703,171 A | 11/1972 | Schiavitto | |
| 3,928,872 A | 12/1975 | Johnson | |
| 4,116,236 A | 9/1978 | Albert | |
| 4,130,115 A | 12/1978 | Taylor | |
| 4,366,813 A | 1/1983 | Nelson | |
| 4,381,769 A | 5/1983 | Prahl | |
| 4,445,505 A | 5/1984 | Labour et al. | |
| 4,450,832 A | 5/1984 | Waddell | |
| 4,522,199 A | 6/1985 | Waddell et al. | |
| 4,632,098 A | 12/1986 | Grundei et al. | |
| 4,727,862 A * | 3/1988 | Waddell | A61F 5/02 |
| | | | 602/16 |
| D298,560 S | 11/1988 | Kitamura | |
| 5,139,477 A | 8/1992 | Peters | |
| 5,399,153 A | 3/1995 | Caprio, Jr. et al. | |
| 5,512,039 A | 4/1996 | White | |
| 5,729,867 A * | 3/1998 | Carmichael | E04B 2/7429 |
| | | | 16/225 |
| 5,730,710 A | 3/1998 | Eichhorn et al. | |
| 5,743,866 A * | 4/1998 | Bauerfeind | A61F 5/0125 |
| | | | 602/62 |
| 5,823,931 A | 10/1998 | Glimour | |
| 6,238,360 B1 * | 5/2001 | Gildersleeve | A61F 5/012 |
| | | | 602/16 |
| D444,563 S * | 7/2001 | Rodgers | A61F 5/0118 |
| | | | D24/190 |
| 6,336,909 B2 * | 1/2002 | Gildersleeve | A61F 5/012 |
| | | | 602/26 |
| 6,551,264 B1 | 4/2003 | Cawley et al. | |
| 6,557,177 B2 | 5/2003 | Hochmuth | |
| 6,623,439 B2 | 9/2003 | Nelson et al. | |
| 7,011,641 B1 * | 3/2006 | DeToro | A61F 5/0125 |
| | | | 602/16 |
| 7,611,476 B2 * | 11/2009 | Taranow | A61F 5/01 |
| | | | 602/12 |
| 8,043,244 B2 | 10/2011 | Einarsson et al. | |
| D654,181 S * | 2/2012 | Chiang | A61F 5/0123 |
| | | | D24/190 |
| 8,282,588 B2 * | 10/2012 | Ingimundarson | A61F 5/02 |
| | | | 602/16 |
| 8,328,745 B2 * | 12/2012 | Einarsson | A61F 5/0106 |
| | | | 602/16 |
| 8,672,864 B2 * | 3/2014 | Nordt, III | A61F 5/0118 |
| | | | 602/20 |
| 8,911,389 B2 * | 12/2014 | Reinhardt | A61F 5/0109 |
| | | | 602/26 |
| 9,797,439 B2 * | 10/2017 | Masini | E05D 1/00 |
| 10,159,588 B1 * | 12/2018 | Nelson | A61F 5/0106 |
| 10,182,935 B2 * | 1/2019 | Sigurdsson | A61F 5/0109 |
| 10,358,851 B1 * | 7/2019 | Ardelean | E05D 1/02 |
| 10,478,368 B2 * | 11/2019 | Lee | A61H 3/00 |
| 2002/0077574 A1 * | 6/2002 | Gildersleeve | B41M 5/035 |
| | | | 602/16 |
| 2005/0038367 A1 * | 2/2005 | McCormick | A61F 5/0106 |
| | | | 602/26 |
| 2006/0135900 A1 * | 6/2006 | Ingimundarson | A61F 5/0123 |
| | | | 602/26 |
| 2007/0106191 A1 | 5/2007 | Mueller et al. | |
| 2007/0167891 A1 * | 7/2007 | Gramza | A61F 5/0106 |
| | | | 602/5 |
| 2009/0287125 A1 * | 11/2009 | Einarsson | A61F 5/0106 |
| | | | 602/23 |
| 2011/0230807 A1 * | 9/2011 | Groehninger | A61F 5/0111 |
| | | | 602/13 |
| 2015/0057587 A1 * | 2/2015 | Walsh | A61F 5/0125 |
| | | | 602/16 |
| 2015/0182366 A1 | 7/2015 | Takenaka et al. | |
| 2016/0095734 A1 * | 4/2016 | Sigurdsson | A61F 5/0123 |
| | | | 602/26 |
| 2017/0027735 A1 | 2/2017 | Walsh et al. | |
| 2018/0042754 A1 * | 2/2018 | Ingimundarson | A61F 5/0109 |
| 2019/0117428 A1 * | 4/2019 | Sigurdsson | A61F 5/01 |

FOREIGN PATENT DOCUMENTS

| | | |
|---|---|---|
| DE | 4222601 A1 | 1/1994 |
| DE | 102009038517 A1 | 6/2011 |
| EP | 0154758 A1 | 9/1985 |
| FR | 2827158 A1 | 1/2003 |
| KR | 100742181 B1 | 7/2007 |
| WO | 2014001748 A2 | 1/2014 |
| WO | 2019185485 A1 | 10/2019 |

OTHER PUBLICATIONS

International Search Report and Written Opinion from PCT Application No. PCT/EP2019/057289, dated Jul. 9, 2019.

* cited by examiner

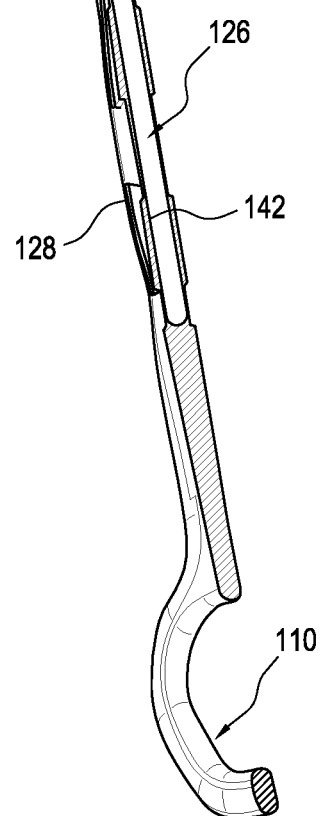
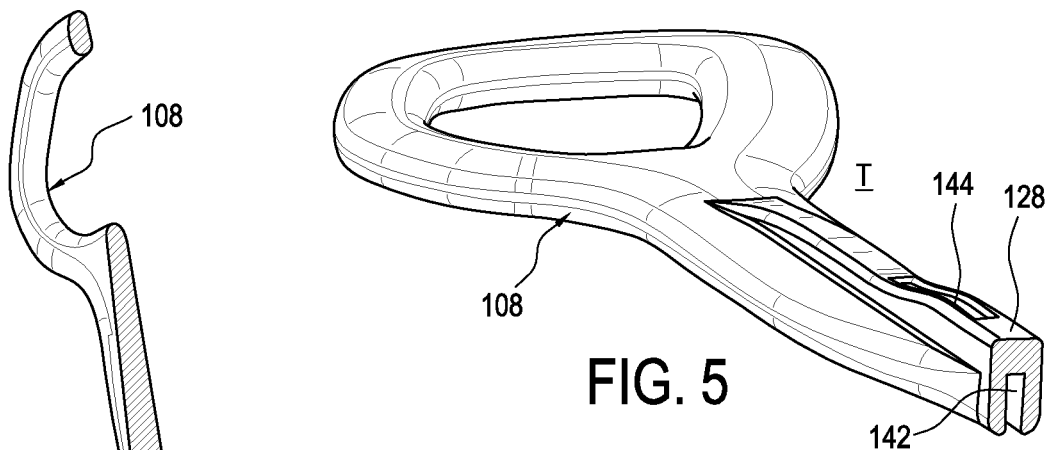
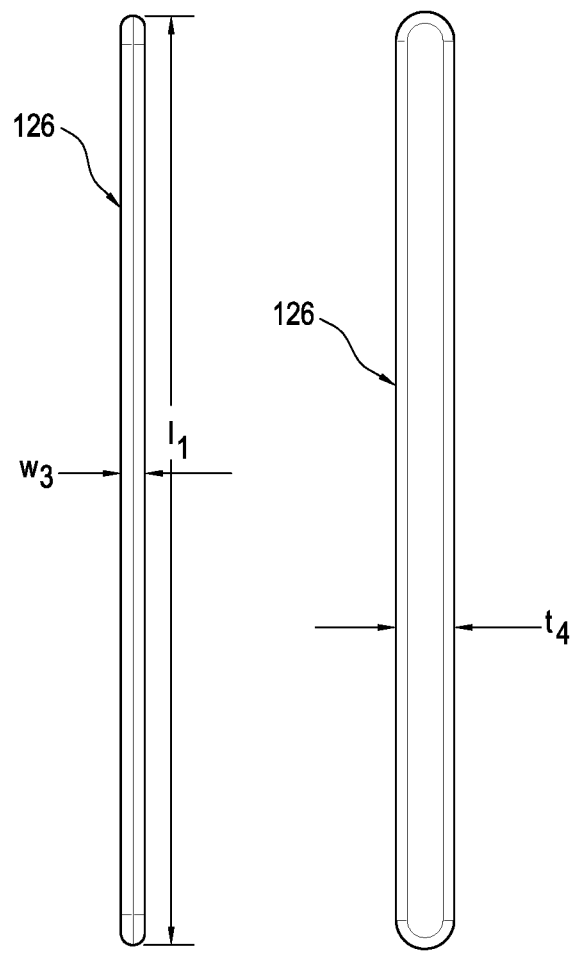
FIG. 4
FIG. 5
FIG. 6A   FIG. 6B

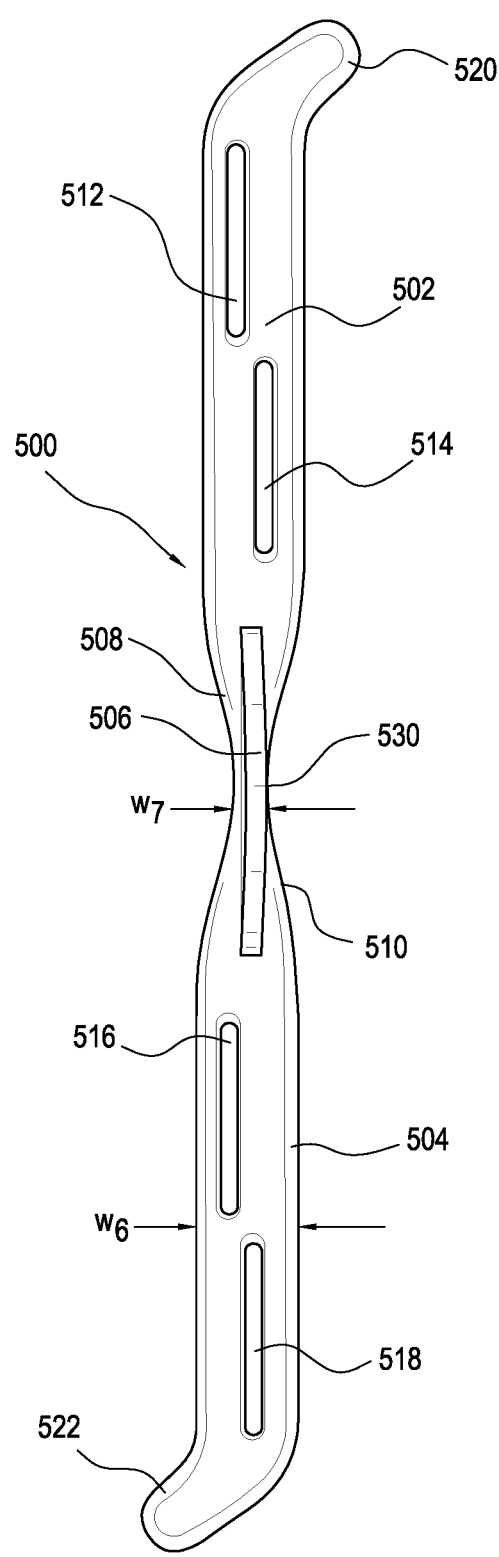
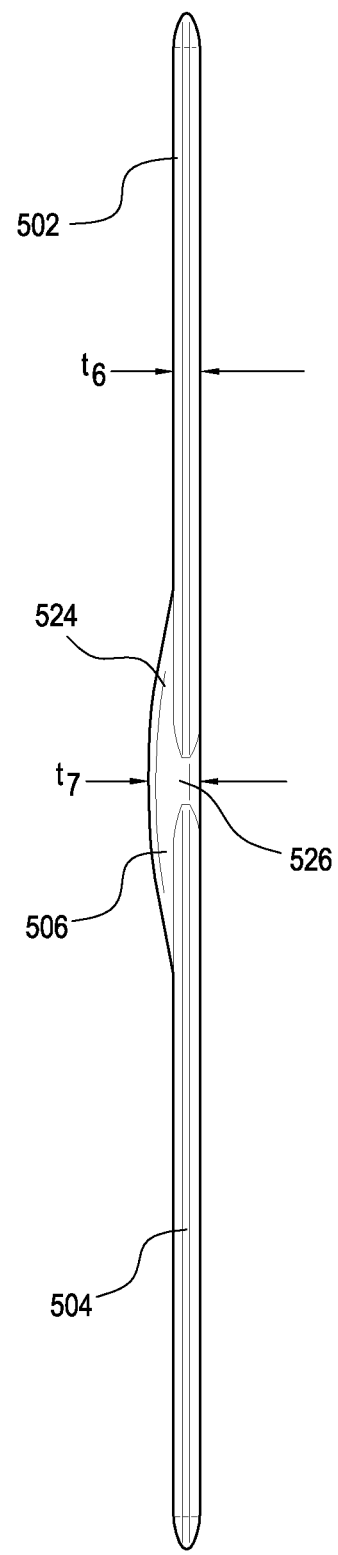
FIG. 9A
FIG. 9B

HINGE FOR ORTHOPEDIC DEVICE

BACKGROUND

Hinges are arranged in orthopedic devices and guide or assist articulation of a joint, such as a knee joint. Some hinges are robust, including multiple parts and structural elements, and facilitate and guide movement of a joint. Such robust hinges may not be necessary in applications of lighter-weight orthopedic devices in that their functional and structural features may be excessive. Such robust hinges may add to weight, cost, bulk, resistance to joint movement, and complexity of an orthopedic device. When such aspects are unwarranted, they are to the disadvantage of a user.

As an alternative to the robust hinges, some lighter-weight orthopedic devices include a lightweight hinge, such as a stay, upright, or flexible bar permitting articulation of the orthopedic device. These hinges permit articulation in a manner that reinforces the orthopedic device upon bending but are less intended for facilitating movement of joint. The lightweight hinges may be embedded or securely enclosed within a panel such as a tubular sleeve in the orthopedic device, and do not engage or couple to other structural features in the orthopedic device, aside from the tubular sleeve.

While these hinges offer joint guidance and support, and retain at least in part the shape of the orthopedic device when defined as a flexible tubular sleeve, they are not adaptable to different characteristics including rigidity, strength, and range or motion control, particularly according to different activity levels. These lightweight hinges may be limited in their use as defining elongate members that have no other function or features aside from opening as a hinge or a stay. There is a problem of lightweight hinges not providing sufficient control or guidance of motion in one or more directions. Additionally, there is a problem of existing lightweight hinges not adapting to the dynamic shape of a user's lib, especially between flexion and extension, while still providing needed strength and effectively cooperating with other elements of an orthopedic device, such as a compressive sleeve.

SUMMARY

Embodiments of a hinge for an orthopedic device provided herein overcome the problems of existing hinges by offering a hinge made from a light and flexible material for optimum shape and fit. In an example, the hinge may be adaptable to an orthopedic device, such as in a compressive knee sleeve requiring a tight-fitting form and streamlined outline. The hinge may further streamline the structure in a compressive orthopedic device by providing means for mounting straps, for example in openings, slots and retainers, and by providing a multi-purpose structure that can guide, facilitate and limit bending within an angular range, and offering a structure for repeated use of a strap for securing and utilizing the orthopedic device on a user. The means for mounting straps can be arranged to direct straps in predetermined directions.

Contrary to many conventional hinges which comprise discrete components, the hinge of the disclosure preferably includes a monolithic hinge body formed from a single material and continuously extends without interruption from a first end to a second end of the hinge. The single material structure may be formed from a polymeric material that may be less hard than metal materials as found in conventional hinges, and necessitates no moving parts and fasteners. The single material structure may be compliant and adapted to flexibly bend not just within an angular range, but also transversely relative to a neutral longitudinal axis of a leg or joint in extension to contour longitudinally end to end to a variable radius of a user's limb, such as in an upper leg (including a thigh) and lower leg (including a calf). The gentle adaptation of the hinge to the user's leg enables a better and closer fit of the orthopedic device on the user.

The articulating portion of the hinge may be reinforced, and may be stiffer at an articulating section to provide angular control of a joint. Because the hinge has a single hinge body, it can be adapted and formed according to different limb lengths, and strengthened and stiffened with variable resiliency or elasticity from longitudinal end to end. The articulating section preferably protrudes minimally from the orthopedic device, and occupies a minimal space over the user's leg. Advantageously, the articulating section minimizes substantial rigid structure along the medial and lateral sides of the orthopedic device, which does not or minimally interferes with the opposing knee of the user or the natural motion of the leg. This allows the orthopedic device to fit snugly to the leg, while conforming to the shape of the leg and offering assistance to the natural motion of the knee between extension and flexion.

According to an embodiment, a hinge includes a hinge body forming an articulating section extending between first and second ends of the hinge. The hinge body is adapted to bend from a neutral axis when the first and second ends are parallel to an angular range in which the first end is arranged among a plurality of angles within the angular range relative to the second end. The articulating section has an adjustable floating center variable radius within the angular range because the variable radius changes according to flexion of the hinge.

The hinge body may define a receptacle along the articulating section. An insert is arranged for insertion into the receptacle, and can modify the stiffness of the hinge in the angular range. The insert is preferably arranged parallel to the neutral axis. The insert may have an elongate shape toward a length of the insert, with a greater thickness relative to a width of the insert. In this manner, a curvature of the insert occurs along the width, and into the thickness of the insert, thereby facilitating bending while maintaining sufficient strength according to repeated use.

Properties of the insert may be selected according to the desired properties at the articulating section. The insert may be more resilient than the hinge body with elastic properties greater than the articulating section, to provide spring-back from the angular range to return the hinge to the neutral axis. The insert may be selected according to a stiffness to modify stiffness of the articulating section. The insert may be formed from a different material than the hinge body, or may be from the same material of the hinge body, but is selected according to its properties and intended benefits imparted to the articulating section. The insert may be removable from the hinge body to switch between different inserts, or the properties of the hinge provided by the absence of the insert may be desirable. The hinge body may define a slot through which the insert may be applied to and removed from the receptacle.

As the hinge body may be continuously formed, it is preferably a single piece of injection molded plastic, longitudinally elongated. The hinge body defines an asymmetric structure because it has localized regions providing different functions for both articulation and strength along the longitudinal length. Aside from rings or strap slots, the hinge body may form a rib protruding from a base thickness of the hinge body at least along the articulating section in the longitudinal direction of the hinge body. The rib may form a maximum thickness in a middle of the articulating section and resist articulation within the angular range or reinforce the articulating section while facilitating bending. The rib may taper in height toward first and second ends to the base thickness.

In supplement to or replacing the rib, the hinge body may have a first width transverse to the neutral axis and outside the articulating section, and a second width in the articulating section that is more narrow than the first width. The hinge body may define include first and second struts arranged on opposed ends of the articulating section. The first and second struts may have a first width, with the articulating section between the first and second struts and having a second width more narrow than the first width. There may be a transition from the first width to the second width whereat the width gradually tapers from the first width to the second width. The second width may be defined in a region of the articulating section elongate along the longitudinal length of the hinge body, and the rib may coincide with the second width to maintain strength of the articulating section while permitting flexibility by the narrower second width.

As an orthopedic device, the hinge may be combined with a tubular sleeve that can compressively secure about a limb. The tubular sleeve may be formed from a textile panel. The hinge may be secured on the tubular sleeve or in a pocket or other suitable retaining features for securing the hinge onto or within the tubular sleeve. In an orthopedic device forming a knee support, the hinge is adapted to bend toward an anterior side of the knee support, leaving a posterior recess on the posterior side of the knee support. The textile panel may be reinforced with a supplementary panel retaining the hinge between the supplementary panel and the textile panel, and being contoured similarly to a profile of the hinge without substantially protruding outwardly from the orthopedic device. Straps may secure to the hinge, and extend about or over the orthopedic device, with the hinge being rigid compared to the textile panel. The hinge may be provided with other types of orthopedic devices as considered useful, and may be adapted accordingly.

By providing the hinge for an orthopedic device according to the disclosure, the hinge provides needed strength and stability to the affected joint of the user, while dynamically conforming to the limb's changing dimensions through flexion and extension, and while cooperating with other components of the orthopedic device, e.g. the compressive tubular sleeve. These functions—dynamic accommodation of the limb, strength and support, and cooperation—are harmonized by the hinge of the disclosure, with no function being sacrificed for another as in existing hinges.

Additional features and advantages of the disclosure will be set forth in the description that follows, and in part will be obvious from the description, or may be learned by the practice of the disclosure. The features and advantages of the disclosure may be realized and obtained with the instruments and combinations particularly pointed out in the appended claims. These and other features of the present disclosure will become more apparent from the following description and appended claims or may be learned by the practice of the disclosure as set forth.

BRIEF DESCRIPTION OF THE DRAWINGS

FIG. 4 is a perspective cross-sectional view of the hinge in FIG. 2 taken along line IV-IV.
FIG. 5 is a perspective cross-sectional view of the hinge in FIG. 2 taken along line V-V.
FIG. 6A is a side elevational view of an insert in the hinge of FIG. 2.
FIG. 6B is a front elevational view of the insert of FIG. 6A.
FIG. 9A is a front plan view of another embodiment of a hinge.
FIG. 9B is an elevational view of the hinge of FIG. 9A.

In the figures, similar elements are provided with similar reference numbers. The drawing figures are not drawn to scale, or proportion, but instead are drawn to provide a better understanding of the components, and are not intended to be limiting in scope, but provide exemplary illustrations.

DETAILED DESCRIPTION OF VARIOUS EMBODIMENTS

A. Overview

Figure 1:
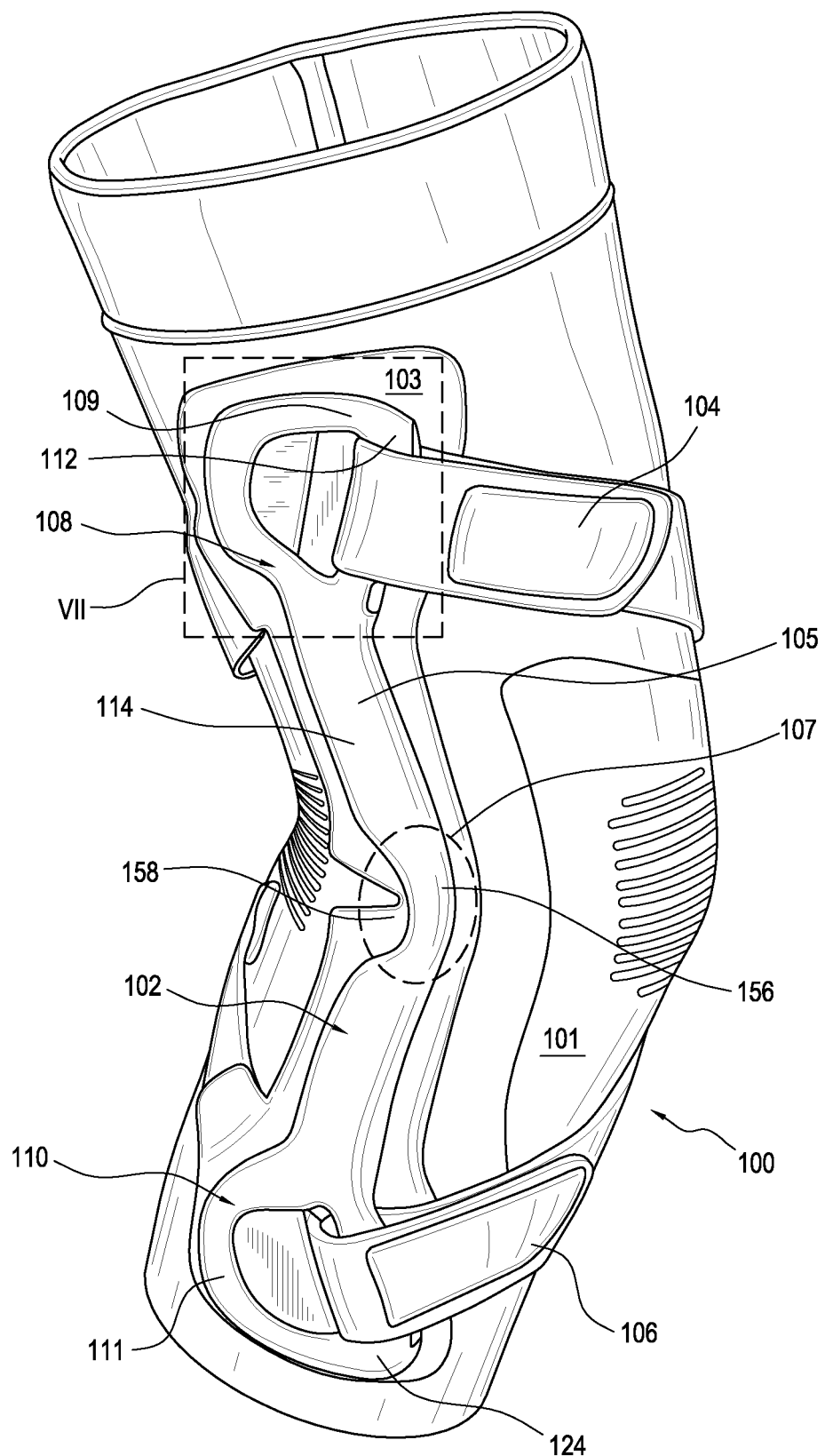
FIG. 1 is a perspective view of an orthopedic device including an embodiment of a hinge.
Figure 2:
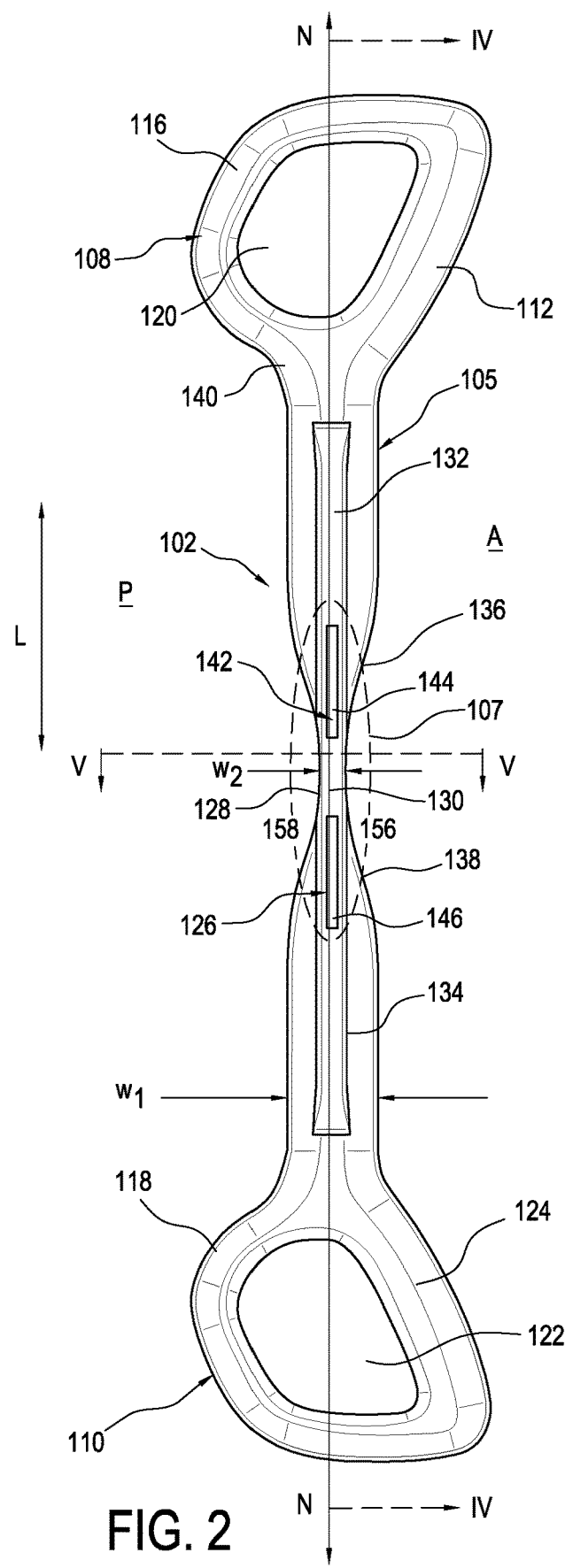
FIG. 2 is a plan view of the hinge of FIG. 1.
Figure 3:
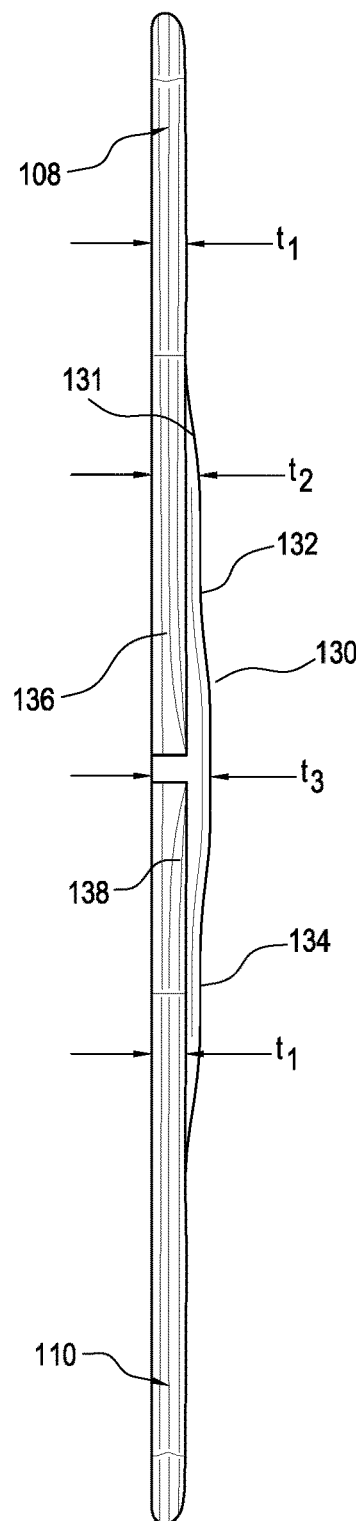
FIG. 3 is a side elevational view of the hinge of FIG. 2.

While the disclosure is susceptible to various modifications and alternative constructions, certain illustrative embodiments are in the drawings and are described below. It should be understood, however, there is no intention to limit the disclosure to the specific embodiments disclosed, but on the contrary, the intention covers all modifications, alternative constructions, combinations, and equivalents falling within the spirit and scope of the disclosure.

B. Environment and Context of Embodiments

Embodiments of the hinge described herein may be provided in an orthopedic device of the type discussed in U.S. patent application Ser. No. 15/672,593, filed on Aug. 9, 2017, published as U.S. patent application publication no. 2018/0042754, on Feb. 15, 2018, and incorporated herein by reference.

For further ease of understanding the embodiments of an orthopedic device in the exemplary form of a textile support for treating complications of the knee and variants as disclosed, a description of a few terms is necessary.

As used herein, the term "flexion" should denote a condition in which a limb, for example a leg, is bent at an articulating joint, such as a knee. The term "extension" is intended to denote a condition in which a limb, for example a leg, is unbent or straightened at an articulating joint, such as a knee. The term "stiffness" has its ordinary meaning as the degree of resistance of an elastic body to deflection or deformation by an applied force, and more particularly to bending between end points in the context of a hinge.

The terms "rigid," "flexible," "compliant," and "resilient" may distinguish characteristics of portions of certain features of the hinge. The term "rigid" should denote that an element of the device is generally devoid of flexibility. Within the context of features that are "rigid," it is intended to indicate that they do not lose their overall shape when force is applied, and may break if bent with sufficient force. The term "flexible" should denote that features are capable of repeated bending such that the features may be bent into retained shapes or the features do not retain a general shape, but continuously deform when force is applied.

The term "compliant" may qualify such flexible features as generally conforming to the shape of another object when placed in contact therewith, via any suitable natural or applied forces, such as gravitational forces, or forces applied by external mechanisms. The term "resilient" may qualify such flexible features as generally returning to an initial general shape without permanent deformation. As for the term "semi-rigid," this term may be used to connote properties of support members or shells that provide support and are freestanding; however, such support members or shells may have some degree of flexibility or resiliency. The term "elastic" may connote stretchability, and the term "semi-elastic" connotes various degrees of elasticity as compared to the term "inelastic" which may mean devoid or substantially devoid of any elasticity.

C. Various Embodiments of the Hinge and Association with an Orthopedic Device FIG. 1 depicts an orthopedic device 100 having a tubular support 101 forming a generally tubular shape. The tubular support 101 is preferably functionally knit and may comprise different zones of varying knitted patterns or formations, and is not limited to being formed from a knitted material; rather it can be formed from a foam or other suitable material used in orthopedic devices. The tubular support 101 may be supplemented with a supplementary panel or panels 103 that correspond to a hinge 102, the hinge 102 extending longitudinally between first and second ends 109, 111, and the tubular support 101 may form a pocket or other retaining structure for the hinge 102.

In this embodiment, the orthopedic device 100 includes straps 104, 106 tethered to first and second, in this instance upper or lower, respectively, rings 108, 110 formed by the hinge 102. More particularly, the straps 104, 106 extend about a forward portion 112 of the first and second rings 108, 110, toward an anterior side A of the orthopedic device 100, and can be pulled against the forward portion 112 as the straps 104, 106 are tensioned. The straps 104, 106 may return to one of the first and second rings 108, 110 on or from a posterior side P of the orthopedic device 100, such that the first and second rings 108, 110 can retain a plurality of strap ends extending in opposing or at least different directions. As shown, the straps 104, 106 may secure directly to the orthopedic device 100, such as by being secured to the tubular support 101 or supplementary panel 103.

The hinge 102 is preferably retained by the orthopedic device 100 by a hinge cover 114 formed by the supplementary panel 103. The hinge 102 may be removably secured within or by the hinge cover 114, or may be permanently secured by the hinge cover 114. By "permanently" it is meant that one must separate at least a portion of the hinge cover 114 in an irreversible manner to withdraw the hinge 102 from the orthopedic device 100, and "removably" means one can repeatedly remove the hinge 114 from the orthopedic device 100 without irreversible alteration of the hinge cover 114 or the tubular support 101.

FIG. 1 exemplifies how the hinge 102 has an anterior compartment 156 that protrudes anteriorly toward the knee, and a notched posterior compartment 158 that offers a recess opening posteriorly of the knee. In this manner, there is no pinching of the hinge 102, particularly posteriorly, and the structure on the medial and lateral aspects of the knee along the sagittal plane is minimized. Both the anterior and posterior compartments 156, 158, as covered by the hinge cover 114, may have differing or similar arcuate shapes, according to the degree of flexion. Such an arrangement reduces pressure over the knee, while offering structural integrity and conformity of the individual anatomy of a user at the articulating section 107 of the knee according to the means in the articulating section 107 discussed below according to the different embodiments. The hinge cover 114 may be configured according to the shape of the hinge 102 as it moves from extension to flexion, as depicted by the varying shapes of the anterior and posterior compartments 156, 158.

As depicted in FIG. 1, the hinge 102 comprises a hinge body 105 and is arranged to flex within the hinge cover 114 in a manner that minimizes space taken by the hinge 102 at the knee. As referred to herein as the articulating section 107, it is evident that because the hinge 102 has a narrow articulating section 107, there is less interference by the hinge 102 where the knee bends. In some conventional braces, a corresponding articulating section may protrude outwardly and risk interference with the user's other knee or any brace the user is wearing. The articulating section of such devices may also fail to accommodate the dynamic dimensions of the knee. In the hinge 102 of the instant disclosure, the articulating section 107 offers the flexion control of the knee without the attendant drawbacks of the prior art.

While depicted as generally being on one of the medial or lateral sides of the tubular support 101, the hinge 102 may be provided on both the medial and lateral sides of the tubular support 101.

As shown in more detail in FIGS. 2-5, the hinge 102 has rear portions 116, 118 of the rings 108, 110 to reinforce forward portions 112, 124, and are configured and dimensioned to distribute pressure exerted by the straps 104, 106 over the leg of the user while the first and second rings 108, 110 maintain their shape despite the forces exerted by the straps 104, 106. The hinge 102 may be symmetric in shape so as to be readily useable on both lateral and medial sides of the orthopedic device 100, or may be asymmetric by accounting for anatomical differences in upper and lower legs. The first and second rings 108, 110 each define an opening 120, 122 to reduce weight and coverage of the first and second rings 108, 110 over the user's leg, and also facilitate reception of a strap 104, 106 therethrough. The first and second rings 108, 110 may or may not be symmetric in shape, individually or collectively.

The hinge 102 defines first and second struts 132, 134 that transition from transitional portions 140 from the rings 108, 110 and have a width w1 along their length. The struts 132, 134 and the rings 108, 110 are preferably semi-rigid or rigid to offer support to the user's leg, and so as not to yield due to tensioning of the straps 104, 106.

An insert 126 may be provided with the hinge 102 to selectively modify the rigidity of the hinge 102. The insert 126 may be elongate as in having length greater than its width, and preferably extends in a longitudinal direction along the length of the hinge. Specifically, the hinge 102 may be formed of a rigid or semi-rigid plastic, such as from an EVA polymer, and its rigidity can be enhanced at least at an articulation area, such as a middle portion 128 of the hinge 102 where it is intended to bend. The middle portion 128 of the hinge 102 is substantially narrowed to a reduced width w2 via tapering first and second transitional portions 136, 138 in comparison to the first and second struts 132, 134 leading from the middle portion 128 to the rings 108, 110. The narrow middle portion 128 facilitates bending of the hinge 102, and forms a receptacle 142 (see FIGS. 4 and 5) that is adapted to receive the insert 126. The insert 126 may be provided in a set of inserts 126 adapted to be received by the receptacle 142, and each insert 126 of the set of inserts may possess different stiffnesses. The insert 126 may have a substantially elongate configuration because the insert 126 extends primarily longitudinally.

While the insert 126 is described as being inserted into the receptacle 142 and selectively removed therefrom, the insert 126 may be permanently placed in the receptacle 142 after the hinge body 105 is formed so that the insert 126 is permanently placed in the receptacle 142. The insert 126 may be inserted into the hinge body 105 as it is cooling so there is at least partial bonding of the material of the insert 126 with the material of the hinge body 105. An adhesive may permanently mount the insert 126 to the hinge body 105. By understanding "permanently," this means that the insert 126 cannot be removed from the hinge body 105 without physically causing damage or deterioration to either the insert 126 or the hinge body 105.

The middle portion 128 may include a raised rib portion 130 at its greatest height or thickness t3 along the middle portion 128, and tapers to a reduced thickness t2 along tapering portions 131 along the first and second struts 132, 134 to its minimal thickness t1 at the first and second rings 108, 110. The middle portion 128 may also define windows 144, 146 through at least the rib portion 130 to show the insert 126. The insert 126 may be color coded depending on its stiffness or resiliency, and the windows 144, 146 expose the color of the corresponding insert 126 as an indicator to a user of the presence and/or stiffness of the insert 126. The rib portion 130 or ridges formed thereby facilitate bending of the hinge 102 in a sagittal plane, but resist bending in a coronal plane.

The preferred embodiment shows the hinge 102 as being monolithically formed, meaning that it is formed as a single body, without interruptions, and is unitary in shape and function. The hinge 102 may be formed by injection molding from a single mold and material deposited in such single mold, without additionally attaching other features to the hinge 102 after the injection molding of the hinge 102. The monolithic hinge body 105 spans the length of the hinge 102, and while it may be supplemented with the insert 126, the single body of the hinge body 105 can individually serve as a hinge without the insert 126 or any other additional component or adaptation.

The perspective cross-sectional view of FIG. 4 shows the arrangement of the receptacle 142 within the hinge body 105 in the embodiment of FIGS. 1-5. The receptacle 142 is configured to receive the insert 126 in a direction parallel to the neutral axis of the hinge 102, thereby allowing the insert 126 to aid in adjusting the degree of flexion only in desired directions.

Likewise, the perspective cross-sectional view of FIG. 5 shows the spatial configuration of the receptacle 142 in the embodiment of FIGS. 1-5. Receptacle 142 is configured to receive a flat, elongate insert 126 within the raised portion of the hinge body 105, facilitating variable flexion of the hinge 102 and the insert 126 along a width of the insert 126.

FIGS. 6A, 6B show an exemplary insert 126. While not limited to the depicted shape, the insert 126 may be configured and dimensioned to snugly fit within the receptacle 142 formed by the hinge 102. The insert 126 may be formed from a plastic or metal, but regardless of the choice of material should have sufficient resiliency to return to its shape from flexion to extension of the hinge 102. As with the rib portion 130 or ridges of the hinge 102, the insert 126 is configured and dimensioned, and placed in the receptacle 142 correspondingly defined, to facilitate bending in the sagittal plane but resist bending in the coronal plane. The insert 126 has a width w3 substantially less than its thickness t4, which are both substantially less than its length l1. These dimensions facilitate the insert 126 to resist bending in the coronal plane but to be receptive to bending in the sagittal plane.

Figure 7:
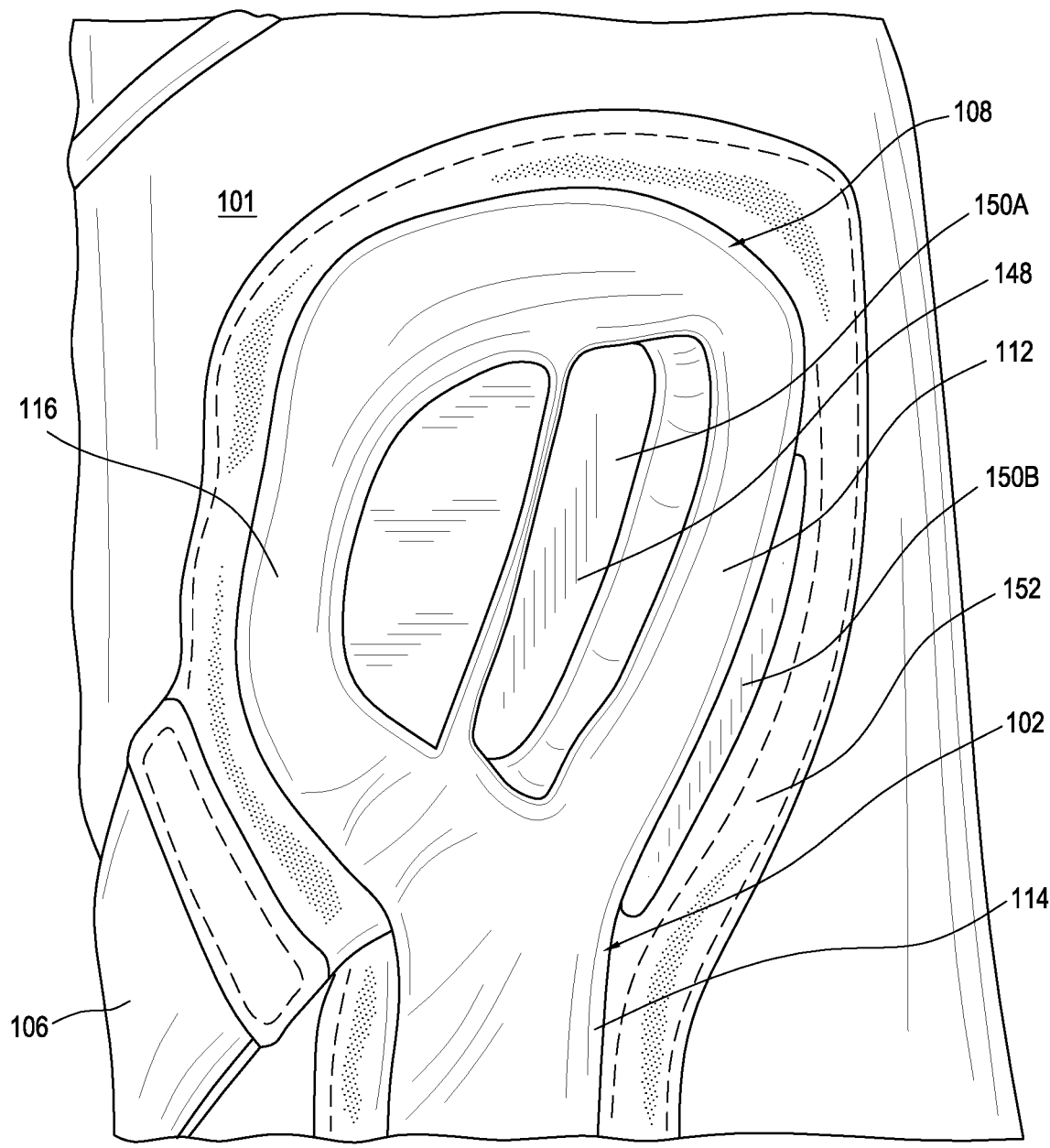
FIG. 7 is a detail view of FIG. 1 without the strap in FIG. 1.

FIG. 7 shows a detail of the hinge 102 secured to the tubular support 101. An opening or slot 148 is defined between or within the ring 108, particularly at the forward portion 112, with the slot 148 having inner and outer sides 150A, 150B. The strap (shown in FIG. 1) is adapted to insert through the slot 148, and fold over itself so it is biased against the forward portion 112. The tubular support 101 may be reinforced proximate the ring 108 which extends from strut 114, and about the hinge 102, with reinforcement elements 152 attached to the tubular body 101 to account for areas in combination with the hinge 102 to resist or reinforce movement or sliding. FIG. 7 also shows that a strap 106 may secure about the rearward portion 116 of the ring 108, thereby forming a multi-directional strap connector.

Figures 8A, 8B, 8C:
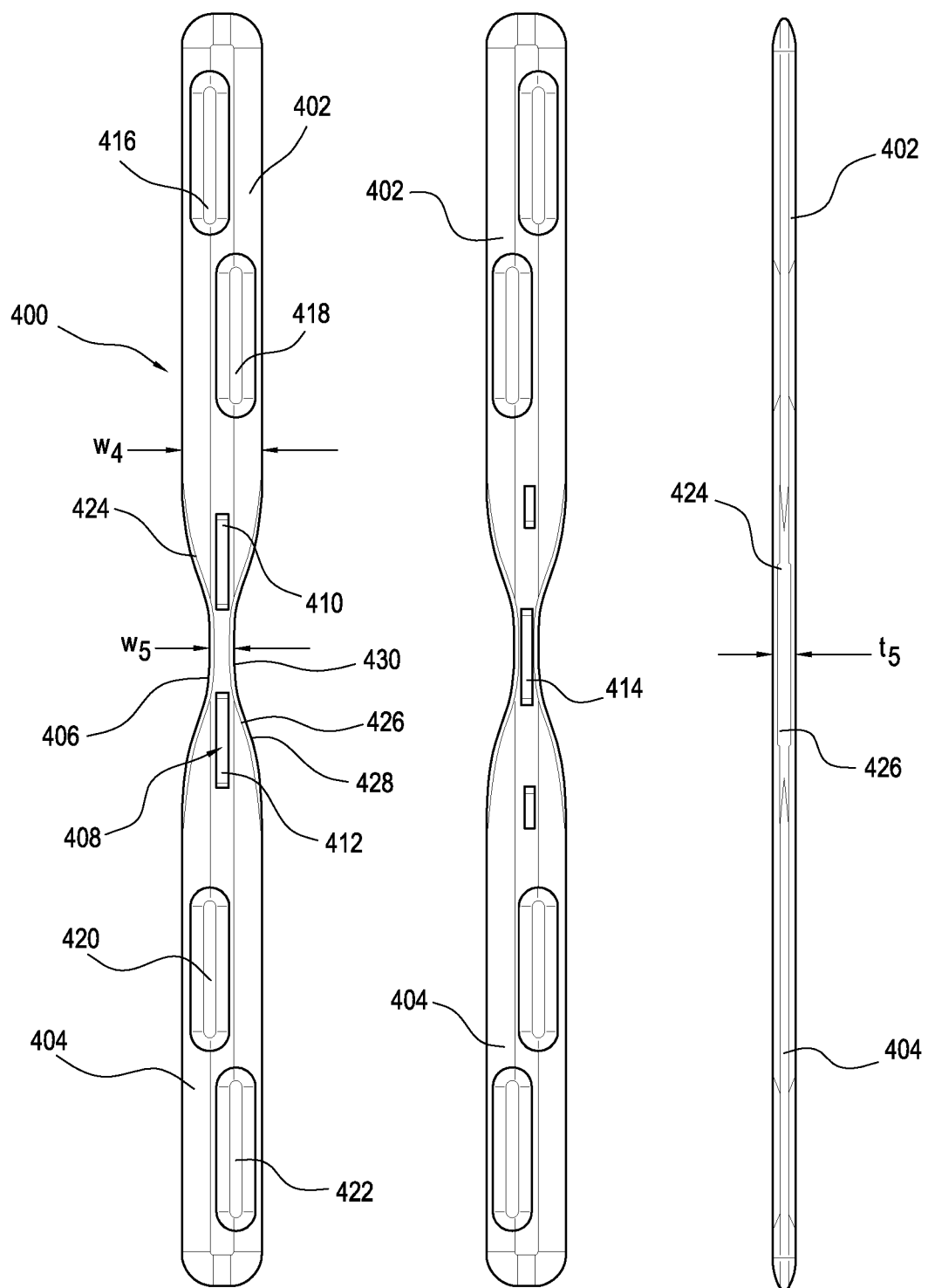
FIG. 8A is a rear plan view of another embodiment of a hinge.
FIG. 8B is a front plan view of the hinge of FIG. 8A.
FIG. 8C is an elevational view of the hinge of FIG. 8A.

FIGS. 8A-8C depict another embodiment of a hinge 400 for an orthopedic device, with the hinge 400 comprising first and second struts 402, 404. Struts 402, 404 are arranged to extend longitudinally and uniformly along the user's leg above and below the knee and have a single width w4. Transition portions 424, 428 attach struts 402, 404 to a middle portion 430 having a narrower width w5 than the width w4 of the struts 402, 404.

Instead of rings 108, 110 of the embodiment of FIGS. 1-5, struts 402, 404 define slots 416, 418, 420, 422 along a length of the struts 402, 404. Slots 416, 418, 420, 422 facilitate the attachment of multiple straps and reduce the size, weight, and material cost of the hinge 400.

As in the embodiment depicted in FIG. 1, the hinge 400 comprises a rib 406 at the middle portion 430, the rib 406 defining a raised portion having a thickness t5 sufficient to receive an insert 426 therein. On one side of the hinge 400, a receptacle 414 is provided to facilitate insertion and retention of the insert 426. On the opposite side of the hinge 400, windows 410, 412 allow a user to see the insert 426 and any indicia provided thereby. In other embodiments, the insert 426 may be placed within the receptacle 414 on the same side as the windows 410, 412.

In contrast to the embodiment of FIGS. 1-5, the hinge 400 of FIGS. 8A-8C may define a center portion of the struts 402, 404 having a uniform thickness t5 along the length of the hinge 400, rather than tapering in thickness from a maximum thickness at the rib and having a minimum thickness at the first and second ends.

FIGS. 9A and 9B depict yet another embodiment of a hinge 500. As in previous embodiments, first and second struts 502, 504 longitudinally extend from a middle portion 530 and attach to the middle portion 530 at transition portions 508, 510. Struts 502, 504 have a width w6 greater than a width w7 of the middle portion 530.

The first and second struts 502, 504 of the embodiment of FIGS. 9A and 9B define wing portions 520, 522 that extend obliquely from the struts 502, 504 over the user's leg proximate the first and second ends of the hinge 500. The wing portions 520, 522 advantageously provide added traction and stability on the underlying tubular support, especially as torque is applied via straps. The wing portions 520, 522 may be securely placed into corresponding receiving structure of an orthopedic device (such as in pockets) to prevent the hinge 500 from popping from the orthopedic device when straps are pulled or upon force. Preferably, the wing portions 520, 522 are directed in opposite directions to the force incurred by the straps. The wing portions 520, 522 may be adapted in a variety of shapes aside from those depicted, including curved, hook or pronged shapes for creating and maintaining traction with the orthopedic device, as in a textile panel.

As in the embodiment of FIGS. 8A-8C, struts 502, 504 define strap slots 512, 514, 516, 518 extending longitudinally between first and second ends of the hinge 500. Slots 512, 514, 516, 518 are configured to support one or more straps around the underlying tubular support and the user's leg and reduce the size, weight, and material cost of the hinge 500. A skilled artisan will understand that more or fewer slots may be provided, and in different locations.

Struts 502, 504 have a thickness t6 that is less than a thickness t7 of a rib 506 defined at the middle portion 530. The greater thickness t7 of the rib 506 accommodates an insert 526, allowing a user or clinician to vary the stiffness of the hinge 500 as necessary. The rib 506 may be in supplement to or in place of an insert. Variations of the hinge 500 may be adapted with a receptacle for placement of an insert, or any of the embodiments herein may have an articulating section reinforced with a bolstered thickness, as depicted in FIG. 9B. Areas outside of the rib 506 may be modified accordingly to facilitate bending or localizing bending of the hinge 500 at the articulating section in correspondence with the rib 506.

Figure 10:
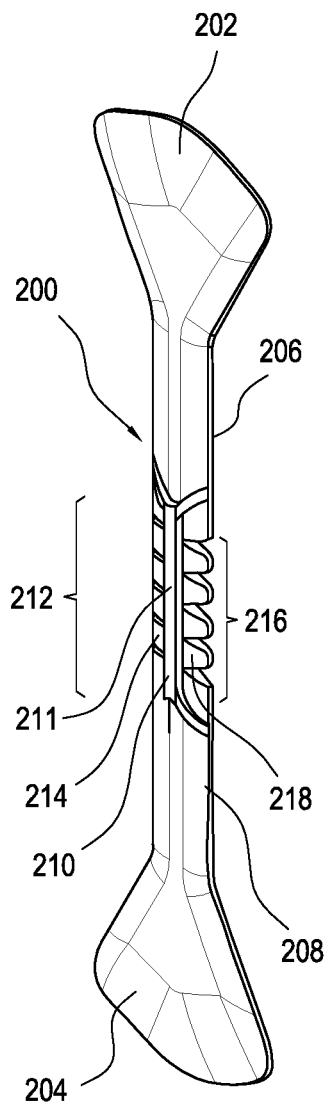
FIG. 10 is a perspective view of another embodiment of a hinge.

FIG. 10 depicts another embodiment of a hinge 200, having first and second bolsters 202, 204, extending from first and second struts 206, 208. The bolsters 202, 204 may be provided as stays to the orthopedic device, or may be modified similarly to the rings 108, 110 in the embodiment of FIG. 1. A rib 210 may extend from the struts 206, 208, and reinforce a middle portion 211 of the hinge 200. Straps 232, 234 are configured to extend from bolsters 202, 204 analogous to the extension of straps 104, 106 from rings 108, 110 in the embodiment of FIG. 1, and by so doing secure the tubular support 220 in a comfortable and convenient manner.

Figures 12A, 12B, 12C:
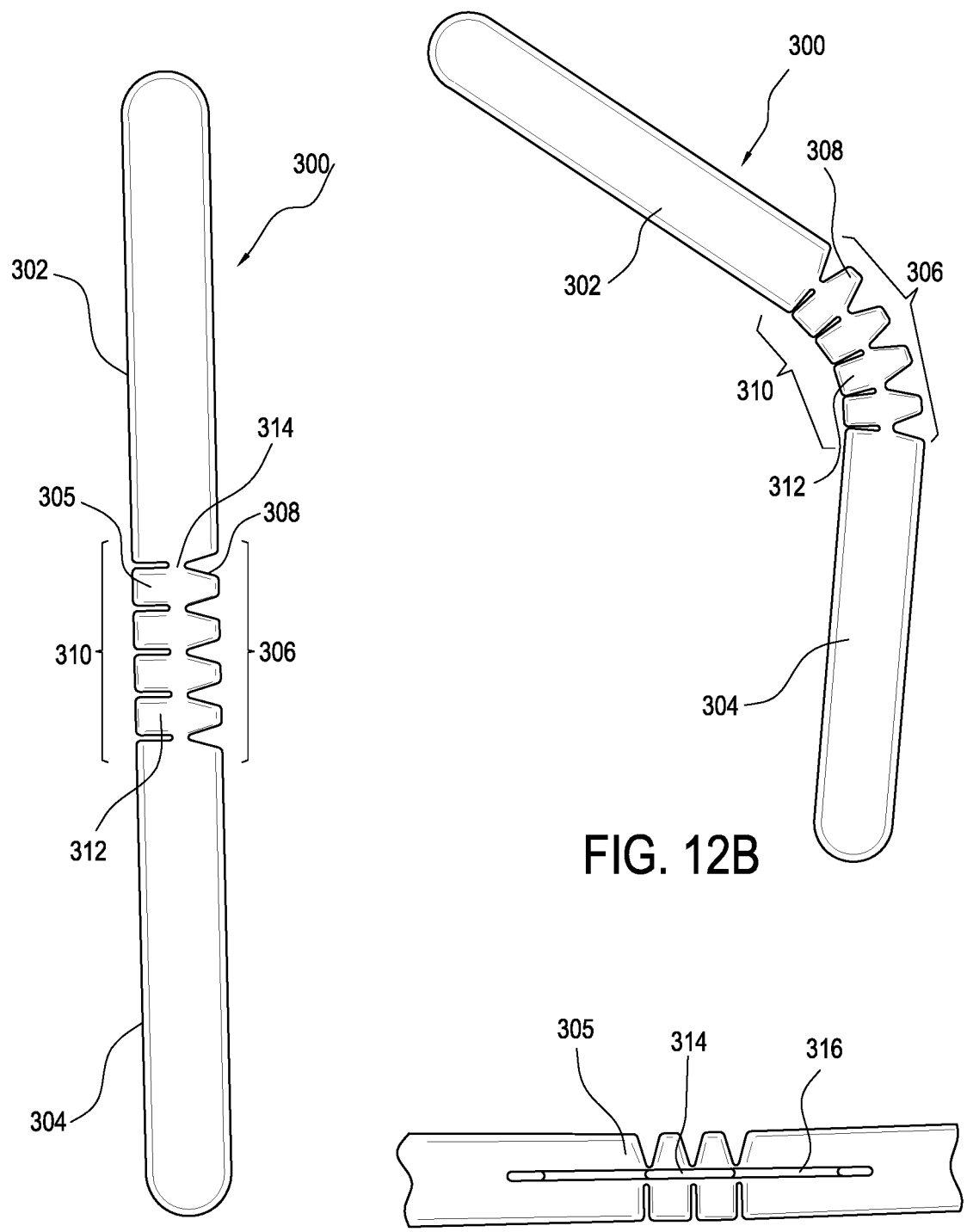
FIG. 12A is a plan view of another embodiment of a hinge in extension.
FIG. 12B is a plan view of the hinge in FIG. 12A in flexion.
FIG. 12C is a plan view of another embodiment of a hinge in extension.

The middle portion 211 defines a first set of hinge elements 212, with each first hinge element 214 adapted to facilitate and reinforce bending of the middle portion 211. The middle portion 211 defines a second set of hinge elements 216, with each second hinge element 218 adapted to facilitate and reinforce bending of the middle portion 211. The second set of hinge elements 216 may be arranged to limit the range of motion of the hinge 200, as depicted in FIG. 12B. The second set of hinge elements 216 are geometrically configured to interfere with one another according to a predetermined degree of bending, which is advantageous to limit the bending of a knee of a user when wearing the orthopedic device.

Figure 11:
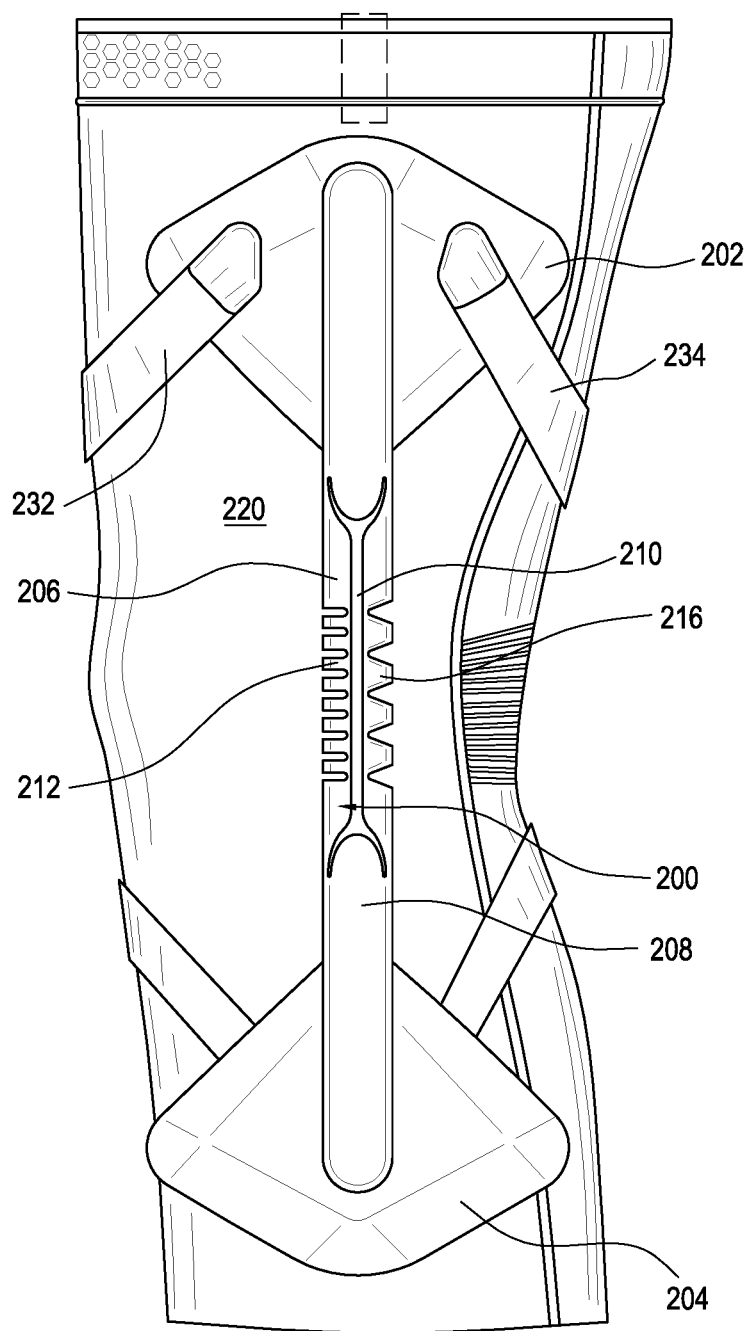
FIG. 11 is a schematic view of another embodiment of a hinge as part of an orthopedic device.

FIG. 11 depicts an arrangement whereby the bolsters 202, 204 are separate from the struts 206, 208, or are formed in greater size. These bolsters 202, 204 may be thinner than the struts 206, 208 and cover a significant portion of the tubular support 220.

FIGS. 12A and 12B illustrate another hinge embodiment 300. In this embodiment, the hinge 300 has first and second struts 302, 304, with a middle portion 305 therebetween. The hinge 300 includes first and second sets of hinge elements 306, 310, each with corresponding first and second hinge elements 308, 312 having predetermined geometrical configurations according to the desired range of motion of the hinge 300. As shown in FIG. 12B, the second set of hinge elements 310 are geometrically configured to limit the bending of the hinge 300 at a predetermined angle of flexion. The first set of hinge elements 306 are arranged to freely permit bending of the hinge 300 to a greater degree than the second set of hinge elements 310.

As shown in FIG. 12C, an insert 314 may be located along the middle portion 305 of the hinge 300, as with the insert 126 of FIG. 1. The insert 314 may be located or is preferably located along the midspan of the hinge 300, and is elongate between the hinge elements 308, 312. A receptacle, retaining elements or slots 316 may be formed by the hinge 300 to hold the insert 314.

It is to be understood that not necessarily all objects or advantages may be achieved under any embodiment of the disclosure. Those skilled in the art will recognize that the hinge for an orthopedic device may be embodied or carried out in a manner that achieves or optimizes one advantage or group of advantages as taught herein without necessarily achieving other objects or advantages as taught or suggested herein.

The skilled artisan will recognize the interchangeability of various disclosed features. Besides the variations described, other known equivalents for each feature can be mixed and matched by one of ordinary skill in this art to construct hinge for an orthopedic device under principles of the present disclosure. It will be understood by the skilled artisan that the features described may be adapted to other types of hinges and/or orthopedic devices. Hence this disclosure and the embodiments and variations thereof are not limited to hinges for soft knee braces, but can be utilized in any hinge for any orthopedic device.

Although this disclosure describes certain exemplary embodiments and examples of a hinge for an orthopedic device, it nevertheless will be understood by those skilled in the art that the present disclosure extends beyond the specifically disclosed hinge embodiments to other alternative embodiments and/or uses of the disclosure and obvious modifications and equivalents thereof. It is intended that the present disclosure should not be limited by the particular disclosed embodiments described above, and may be extended to other hinges for other orthopedic devices and supports, and other applications that may employ the features described herein.

The invention claimed is:
1. A hinge for an orthopedic device comprising:
   a monolithic hinge body having:
      a substantially flat plate having a longitudinal length extending along a neutral axis from a first end to a second end, a first width transverse to the neutral axis at the first end and the second end, and a thickness transverse to the first width;
      an articulating section extending between the first end to the second end, wherein the first width of the plate at the first end and the second end is greater than a second width of the plate in the articulating section;

a rib protruding from the plate along the neutral axis; and a receptacle extending into the plate and the rib along the neutral axis; and a stiffening insert configured for insertion into the receptacle;

wherein the hinge body is adapted to bend through an angular range from a first position such that the first end and second end are aligned with the neutral axis and a second position such that one of the first end and second end is at an angle with respect to the neutral axis and the stiffening insert modifies the stiffness of the hinge in the angular range.

2. The hinge of claim 1, wherein the hinge body is continuously formed from a single material from the first end to the second end of the hinge.

3. The hinge of claim 1, wherein the hinge body continuously extends without interruption from the first end to the second end of the hinge in a longitudinal direction along the neutral axis.

4. The hinge of claim 1, wherein the hinge body forms a first ring at the first end of the hinge.

5. The hinge of claim 4, wherein the first ring defines a first ring portion on an anterior side of the hinge, and a second ring portion on a posterior side of the hinge, the first ring portion having a different shape than the second ring portion.

6. The hinge of claim 5, wherein the first ring portion defines a generally elongate bar, and the second ring portion forms a curvature.

7. The hinge of claim 1, wherein the rib protruding from the plate extends along an entire length of the articulating section in a longitudinal direction along the neutral axis.

8. The hinge of claim 7, wherein the rib forms a maximum thickness in a middle of the articulating section and resists articulation within the angular range.

9. The hinge of claim 8, wherein the rib tapers in height from the middle of the articulating section toward the first end and the second end.

10. The hinge of claim 1, wherein the hinge body tapers from the first width transverse to the neutral axis to the second width in the articulating section.

11. The hinge of claim 1, wherein the hinge body includes a first strut and a second strut each arranged on opposed ends of the articulating section, the first strut and the second strut having the first width transverse to the neutral axis, and the articulating section having the second width.

12. The hinge of claim 11, wherein the hinge body tapers from the first width to the second width.

13. The hinge of claim 11, wherein the second width is located generally equidistant between the first end and the second end of the hinge body, and extends a length longitudinally along the neutral axis less than an entirety of the articulating section.

14. The hinge of claim 1, wherein the insert has an elongate shape.

15. The hinge of claim 1, wherein the insert has a greater stiffness than the articulating section of the hinge body.

16. The hinge of claim 1, wherein the hinge body is symmetric.

17. The hinge of claim 1, wherein the hinge body is asymmetric.

18. The hinge of claim 1, wherein the articulating section forms at least one slot for removably placing the insert within the receptacle.

* * * * *